(12) United States Patent
Bian et al.

(10) Patent No.: US 8,652,540 B2
(45) Date of Patent: Feb. 18, 2014

(54) METHOD OF USING RHEIN FOR TREATING FIBROTIC CONDITIONS AND TUMORS

(71) Applicant: Hong Kong Baptist University, Kowloon (HK)

(72) Inventors: Zhaoxiang Bian, Hong Kong (HK); Siu Wai Tsang, Hong Kong (HK); Aiping Lu, Hong Kong (HK); Haitao Xiao, Hong Kong (HK); Hongyan Qin, Hong Kong (HK); Albert Sun-Chi Chan, Hong Kong (HK); Hongxi Xu, Hong Kong (HK); Shilin Chen, Hong Kong (HK); Dajian Yang, Hong Kong (HK)

(73) Assignee: Hong Kong Baptist University, Kowloon Tong, Kowloon (HK)

( * ) Notice: Subject to any disclaimer, the term of this patent is extended or adjusted under 35 U.S.C. 154(b) by 0 days.

(21) Appl. No.: 13/831,990

(22) Filed: Mar. 15, 2013

(65) Prior Publication Data
US 2013/0323329 A1    Dec. 5, 2013

Related U.S. Application Data

(60) Provisional application No. 61/655,472, filed on Jun. 4, 2012.

(51) Int. Cl.
*A01N 65/00*    (2009.01)
(52) U.S. Cl.
USPC ........................................................ 424/725
(58) Field of Classification Search
None
See application file for complete search history.

(56) References Cited

U.S. PATENT DOCUMENTS

2006/0058392 A1    3/2006    Charbit et al.

OTHER PUBLICATIONS

Apte et al., "Periacinar stellate shaped cells in rat pancreas: identification, isolation, and culture", GUT, 1998, 43(1), 128-133.
Apte et al., "Pancreatic stellate cells are activated by proinflammatory cytokines: implications for pancreatic fibrogenesis" GUT, 1999, 44(4), 534-541.
Cong et al., "ER Stress, P66shc, and P-Akt/Akt Mediate Adjuvant-Induced Inflammation, Which Is Blunted by Argirein, a Supermolecule and Rhein in Rats", Inflammation, 2012, 35(3), 1031-40.
DiMagno et al., "Chronic Pancreatitis", Curr Opin Gastroenterol, 2011, 27 (5), 452-459.
Erkan et al., "StelaTUM: current consensus and discussion on pancreatic stellate cell research", GUT, 2012, 61(2), 172-178.
Qin Hu et al., "In vitro anti-fibrotic activities of herbal compounds and herbs". Nephrol Dial Transplant, 2009, 24(10), 3033-3041.
Bing-Lang Ma et al: , "Effective constituents in Xiexin Decoction for anti-inflammation", Journal of Ethnopharmacology, 2009, 125(1),151-156.
Makoto Otsuki et al. "AnimalModels of Chronic Pancreatitis", Gastroenterology Research and Practice, 2010, 2010 (2010), 8 pages.
P A Phillips et al., "Cell migration: a novel aspect of pancreatic stellate cell biology", GUT, 2003, 52, 677-682.
Eric Schneider et al., "Identification of mediators stimulating proliferation and matrix synthesis of rat pancreatic stellate cells", 2001, 281, p. C532-C543.
Gisela Sparmann et al., "Generation and characterization of immortalized rat pancreatic stellate cells", The American Journal of Physiology-Gastrointestinal and Liver Physiology, 2004, 287(1), p. G211-G219.
Dona Tang et al. "Persistent activation of pancreatic stellate cells creates a microenvironment favorable for the malignant behavior of pancreatic ductal adenocarcinoma", International Journal of Cancer, 2013, 132(5), 993-1003.
H Witt, "Chronic pancreatitis and cystic fibrosis" GUT, 2003, 52(suppl II), p. ii31-ii41.
Phillips P. Pancreatic stellate cells and fibrosis. In: Grippe PJ, Munshi HG, editors. Pancreatic Cancer and Tumor Microenvironment. Trivandrum (India): Transworld Research Network; 2012. Chapter 3.
Reagan-Shaw et al., FASEB J. Mar. 2008;22(3):659-61.

*Primary Examiner* — Michael Meller
(74) *Attorney, Agent, or Firm* — Ella Cheong Hong Kong; Sam T. Yip (57) ABSTRACT

The present invention relates to a method of using an anthraquinone derivative namely 9,10-Dihydro-4,5-dihydroxy-9,10-dioxo-2-anthracenecarboxylic acid, or known as Rhein, for treating chronic pancreatitis induced fibrosis of the pancreas. More particularly, the present invention relates to a method of using Rhein, its derivatives and/or chemical variants as an anti-fibrotic agent. The present invention particularly relates to the suppression of pancreatic stellate cell activation for the management of chronic inflammatory, fibrotic and tumorigenic pathologies in the pancreas.

5 Claims, 9 Drawing Sheets

METHOD OF USING RHEIN FOR TREATING FIBROTIC CONDITIONS AND TUMORS

CROSS-REFERENCE TO RELATED APPLICATIONS

The present application claims priority of U.S. provisional application No. 61/655,472 filed Jun. 4, 2012, and which the disclosure is hereby incorporated by reference in its entirety.

FIELD OF INVENTION

The present invention relates to a method of using Rhein for treating chronic pancreatitis induced fibrosis of pancreas in a subject in needs thereof. More particularly, the present invention relates to the method of using an anthraquinone derivative, namely 9,10-Dihydro-4,5-dihydroxy-9,10-dioxo-2-anthracenecarboxylic acid, also known as Rhein, as an anti-fibrotic agent. The present invention particularly relates to the suppression of pancreatic stellate cell activation for the management of chronic inflammatory, fibrotic and tumorigenic pathologies in the pancreas of a subject.

BACKGROUND OF INVENTION

Pancreatic fibrosis, a characteristic histopathological feature of chronic pancreatitis (CP), is actually an active dynamic process that results in irreversible morphological scarring of the pancreatic parenchyma. The long-standing or recurrent inflammation of the pancreas is often associated with progressive fibrosis; thus, causes persistent abdominal pain and permanent impairment of pancreatic functions, and eventually leads to a variety of systemic complications including malabsorption and diabetes mellitus. In general, CP is commonly arisen from abnormal or over-consumption of alcohol. Besides inflammation, pancreatic fibrosis can also be idiopathic and hereditary, for example, mutations in genes PRSS1, SPINK1 and CFTR, also contribute to its development as claimed in DiMagno M J, DiMagno E P. Curr Opin Gastroenterol. 2011 September; 27(5):452-9. Several recent studies, such as Witt H. Gut. 2003 May; 52 Suppl2:ii31-41, reported that CP and fibrosis are linked with an increased risk of pancreatic cancer, especially for smokers.

A number of animal models for investigation of pancreatic fibrosis have been employed in order to allow translation to the human situation. Chronic repetitive over-stimulation with the cholecystokinin 8 (CCK8) analogue cerulein (50 μg/kg/intra-peritoneal injection) for an induction of CP is one of the most commonly used approaches, such as in Otsuki M, et al. Gastroenterol Res Pract. 2010; 2010:403295, in rodents. During the development of pancreatic fibrosis under CP conditions, the irreversible morphological scarring of pancreatic parenchyma is a prominent consequence of the active fibrotic process. In fact, the most crucial initiating step of this fibrotic process is the activation of pancreatic stellate cells (PSCs) that are generally localized at the periacinar region of the pancreas. In normal pancreas, PSCs are typically quiescent; however, in injured or fibrotic pancreas, PSCs lose their fat-droplets and transform into myofibroblast-like cells followed by the formation of stress fibers. This transformation process is so-called activation, as reported in Phillips P A, et al. Gut. 2003 May; 52(5):677-82, which can be typically identified by the expression of α-smooth muscle actin (α-SMA or Acta2). Upon tissue injury or inflammation, a variety of pro-fibrotic cytokines and hormonal factors such as transforming growth factor β (TGF-β), interleukin 1β (IL-1β), platelet-derived growth factor (PDGF) and tumor necrosis factor α·(TNF-α) trigger PSC activation, as reported in Erkan M, et al. Gut. 2012 February; 61(2):172-8. Once PSCs are activated and transformed into myofibroblast-phenotype, α-SMA and extracellular matrix (ECM) proteins including collagen I-α1 (COL I-α1) and fibronectin (FN1) are extensively expressed at the areas of active pancreatic fibrogenesis, as reported in Apte M V, et al. Gut. 1998 43: 128-133, Apte M V et al. Gut. 1999 April; 44(4):534-41 and Schneider E, et al. Am J Physiol Cell Physiol. 2001 August; 281(2):C532-43. According to recent studies such as Hu Q, et al. Nephrol Dial Transplant. 2009 October; 24(10):3033-41, TGF-β is suggested as the pivotal mediator involved in nearly all kinds of fibrotic conditions, for instance, hepatic fibrosis, pulmonary fibrosis and pancreatic fibrosis, and potently induces massive production of ECM proteins. Inflammatory disorders, regardless of their stages of acute or chronic, can be evolved with abnormal fibrotic events and accumulation of ECM proteins, and hence result in scarring of tissues that is often irreversible. In fact, the composition of fibrotic scarring is relatively common irrespective of the cause of injury or type of tissue. The progressive fibrotic process eventually leads to permanent destruction of the gland and exocrine and/or endocrine insufficiency. For that reason, the activation and proliferation of PSCs reflects the extent of fibrosis in the pancreas and in turn to be a logical target for therapeutic intervention. The immortalized rat LTC-14 cell line, established by Sparmann G et al in Sparmann G, et al. Am J Physiol Gastrointest Liver Physiol 2004 July; 287(1):G211-9, has been proved to retain the essential characteristics and morphological features of primary PSCs, and therefore this line can serve as an ideal in-vitro model for studying fibrogenesis-related mechanisms. As fibrotic pathologies are triggered or produced by the up-regulation of fibrogenic mediators, particularly α-SMA and TGF-β and the subsequent overwhelmed ECM protein synthesis, agents which can attenuate α-SMA, TGF-β and the sequential production of ECM proteins in LTC-14 cells and in cerulein-induced pancreatic tissues are of potential for treating fibrotic disorders and the associated inflammatory conditions.

It is also known, as reported in Tang D, Wang D, Yuan Z, Xue X, Zhang Y, An Y, Chen J, Tu M, Lu Z, Wei J, Jiang K, Miao Y. Persistent activation of pancreatic stellate cells creates a microenvironment favorable for the malignant behavior of pancreatic ductal adenocarcinoma. Int J. Cancer. 2013 Mar. 1; 132(5):993-1003 that by producing high levels of cytokines, chemotactic factors, growth factors and excessive ECM, PSCs create desmoplasia and a hypoxic microenvironment that promote the initiation, development, evasion of immune surveillance, invasion, metastasis and resistance to chemoradiation of pancreatic ductal adenocarcinoma (PDAC). PDAC is one of the most common malignant tumors with poor prognosis due to extremely high malignancy, low rate of eligibility for surgical resection and chemoradiation resistance. Increasing evidence indicate that the interaction between activated PSCs and PDAC cells plays an important role in the development of PDAC. Therefore, targeting the interaction between PSCs and PDAC cells, and/or by suppressing the activation of PSCs, may represent novel therapeutic approaches to advanced PDAC, especially therapies that target PSCs of the pancreatic tumor microenvironment.

Citation or identification of any reference in this section or any other section of this application shall not be construed as an admission that such reference is available as prior art for the present application.

SUMMARY OF INVENTION

Accordingly, the first objective of the present invention is to provide compounds, from Rhein, as a potential anti-fibrosis drug.

Accordingly, the second objective of the present invention relates to Rhein or extracts from Polygonaceae (rhubarb) as a potential anti-fibrotic agent, and method of using a therapeutically effective amount of Rhein or anthraquinone compound for the treatment and/or alleviation of fibrotic conditions such as pancreatic fibrosis in a subject in needs thereof. Rhein effectively inhibits pro-fibrotic mediators TGF-β and α-SMA and the activation of PSCs. Further, Rhein lessens ECM synthesis, namely type 1 collagen and fibronectin, in a dose-dependent manner in vitro. The attenuation of fibrotic mediators has been also reproduced in vivo in a mouse model of cerulein-induced chronic pancreatitis. Most importantly, oral administration of Rhein shows no adverse effects in the animal study.

In another aspect of the present invention, there is provided a treatment of fibrosis related diseases and/or pancreatitis, which comprises administering thereto an effective amount of compounds from Rhein, their derivatives/chemical variants, or a mixture thereof.

In further aspect of the present invention, there is provided a treatment of tumors related diseases and/or pancreatic ductal adenocarcinoma, which comprises administering thereto an effective amount of compounds from Rhein, their derivatives/chemical variants, or a mixture thereof.

Those skilled in the art will appreciate that the present invention described herein is susceptible to variations and modifications other than those specifically described.

The present invention includes all such variation and modifications. The present invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF DRAWINGS

The above and other objects and features of the present invention will become apparent from the following description of the present invention, when taken in conjunction with the accompanying drawings, in which:

FIG. 3 (A) shows the activation of PSCs in terms of α-SMA-immunoreactivities in pancreatic tissues obtained from different groups (i.e. control, Cerulein and Cer+Rh 6w) of mice by means of fluorescent staining (100×): DAPI staining indicates the number of nuclei whereas anti-α-SMA immunoreativity represents the expression of α-SMA.

FIG. 3 (B) shows the production of collagenous proteins by means of Sirius Red staining, Rhein-treated pancreases are shown to have less ECM collagen production. OD at 540 nm represents the presence of collagen whereas OD at 605 nm represents the presence of non-collagenous proteins. A p-value of less than 0.05 is considered as statistically significant. *$p<0.05$ when comparing with Control group (Con) whereas #<0.05 comparing with Cerulein group.

FIG. 3 (C) shows the expression levels of α-smooth muscle actin (α-SMA) and fibronectin 1 (FN1) by means of Western blotting, Rhein-treated pancreatic tissues are shown to have decreased amount of α-SMA and FN1. Levels of α-SMA and FN1 are normalized to the internal reference β-ACTIN and calculated as fold change over control. A p-value of less than 0.05 is considered as statistically significant. *$p<0.05$ when comparing with Control group (Con) whereas 0<0.05 comparing with Cerulein group.

DETAILED DESCRIPTION OF INVENTION

The present invention relates to an anthraquinone derivative, 9,10-Dihydro-4,5-dihydroxy-9,10-dioxo-2-anthracenecarboxylic acid, also known as Rhein with formula 1:

(1)

the compound of which can be extracted from roots of Polygonaceae (rhubarb) by water extraction and solvent evaporation. According to the Chinese pharmacopoeia, this rhubarb extract which is yellow and crystalline has been serving as a mild laxative agent as well as an astringent since ancient times. In the present invention, the Rhein powder was purchased from Nanjing Zelang Medical Technology Company Limited and was proved with a purity of ≥98%.

Figure 1:
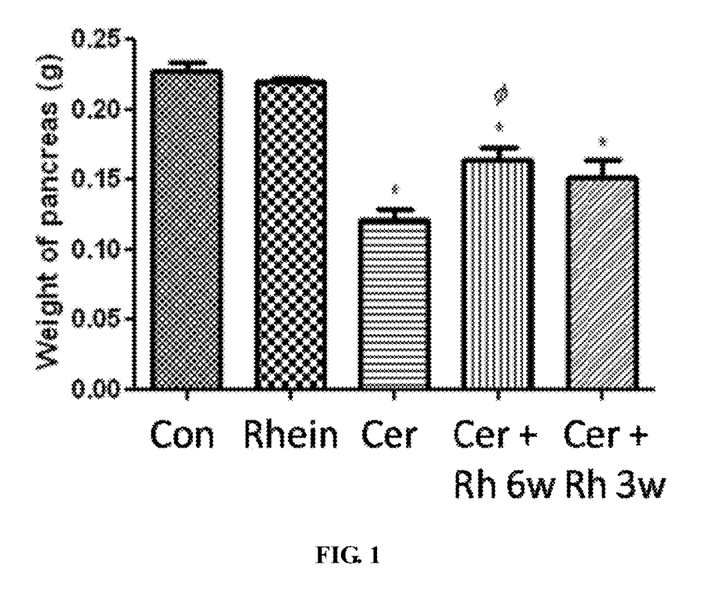
FIG. 1 shows that the decrease of pancreatic weights due to the severe loss of parenchymal acini correlates to the severity of pancreatic fibrosis in mice treated with cerulein. The administration of Rhein results in a significant restoration of pancreatic weight from cerulein-induced pancreatitis. A p-value of less than 0.05 is considered as statistically significant. *$p<0.05$ when comparing with Control group (Con) whereas $\phi<0.05$ comparing with Cerulein group.
Figure 2:
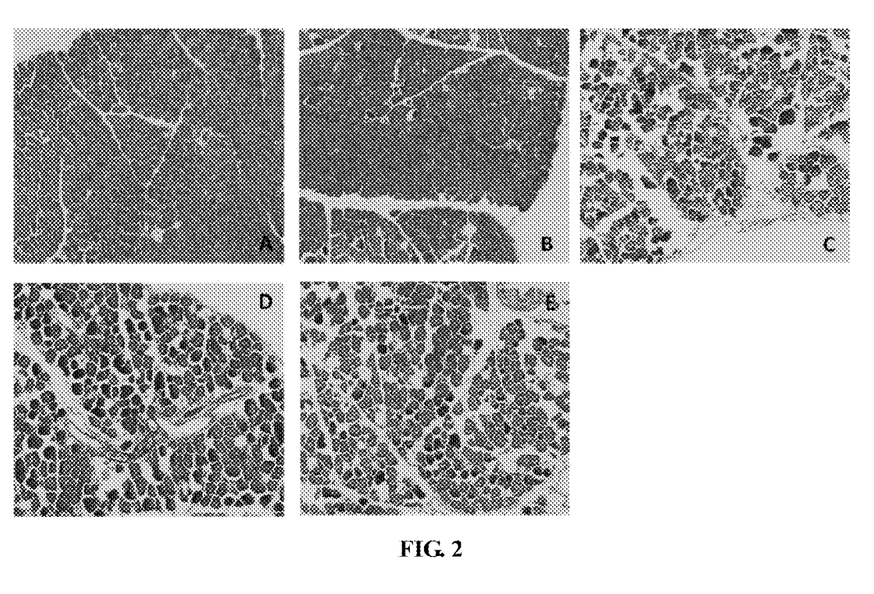
FIG. 2 shows the architecture and morphological alternation in pancreatic tissues of control group, cerulein group and cerulein+Rhein treatment group, by means of H&E staining (100×): (A) control (Con); (B) Rhein (Rh); (C) Cerulein (Cer); (D) Cer+Rh 6w; (E) Cer+Rh 3w.

In one embodiment, the oral administration of Rhein at an adequate dosage of 50 mg/kg/day is shown to significantly ameliorate the severity of pancreatic fibrosis in cerulein-induced mice. In the aspect of histology, CP mice treated with Rhein are shown to have less acinar loss (FIG. 1), lymphocyte infiltration and fibrosis in the pancreatic tissues (FIG. 2). According to the formula for dose translation disclosed in Reagan-Shaw et al. (FASEB J. 2008 March; 22(3):659-61), where the disclosure of which is incorporated herein by reference, the human equivalent dose (HED) of Rhein for adult and child should be 4.05 mg/kg and 6 mg/kg, respectively.

Rhein is not toxic or harmful to animals as the administration of Rhein provides no negative effects on the body weights of the mice as shown in Table 1.

TABLE 1

| Body wt (g) | Con | Rhein | Cer | Cer + Rh 6 wk | Cer + Rh 3 wk |
|---|---|---|---|---|---|
| Mean | 26.06 | 26.10 | 24.05* | 23.98* | 24.07* |
| S.D. | ±0.4195 | ±0.6898 | ±1.155 | ±0.9133 | ±0.7378 |

A p-value of less than 0.05 is considered as statistically significant and S.D. stands for standard deviation.
*p < 0.05 when comparing with Control group (Con).

Cerulein-induced elevated serum levels of TNF-α that are significantly suppressed by the administration of Rhein are shown in Table 2.

TABLE 2

| TNF-α (ng/mL) | Con | Rhein | Cer | Cer + Rh 6 wk | Cer + Rh 3 wk |
|---|---|---|---|---|---|
| Mean | 13.52 | 14.43 | 48.10* | 31.18# | 32.52# |
| S.D. | ±5.575 | ±7.077 | ±9.877 | ±10.45 | ±3.761 |

A p-value of less than 0.05 is considered as statistically significant.
*p < 0.05 when comparing with control where as #p < 0.05 when comparing Cerulein group.

Figure 3A:
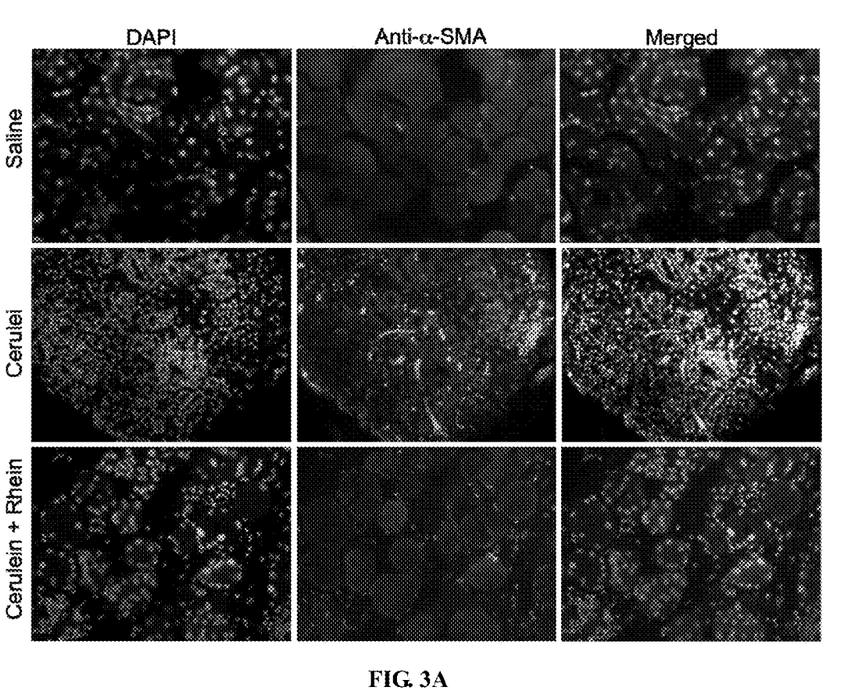
Figure 3B:
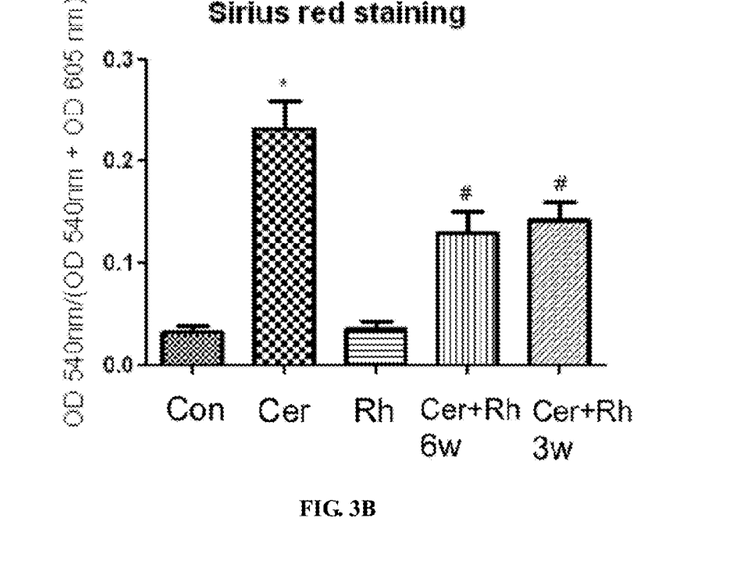
Figure 3C:
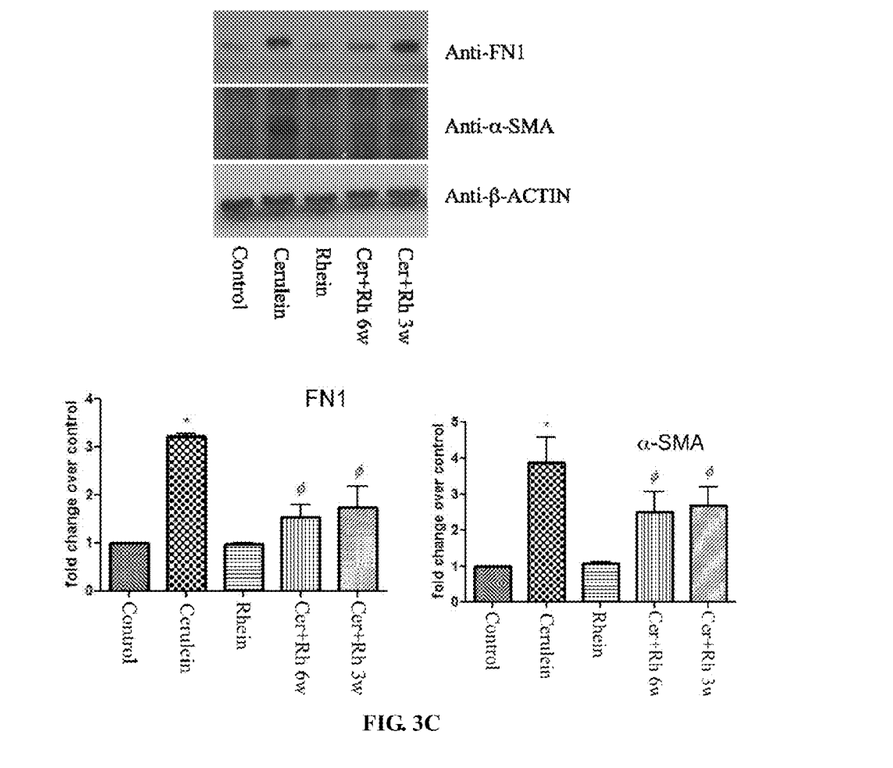
Figure 4:
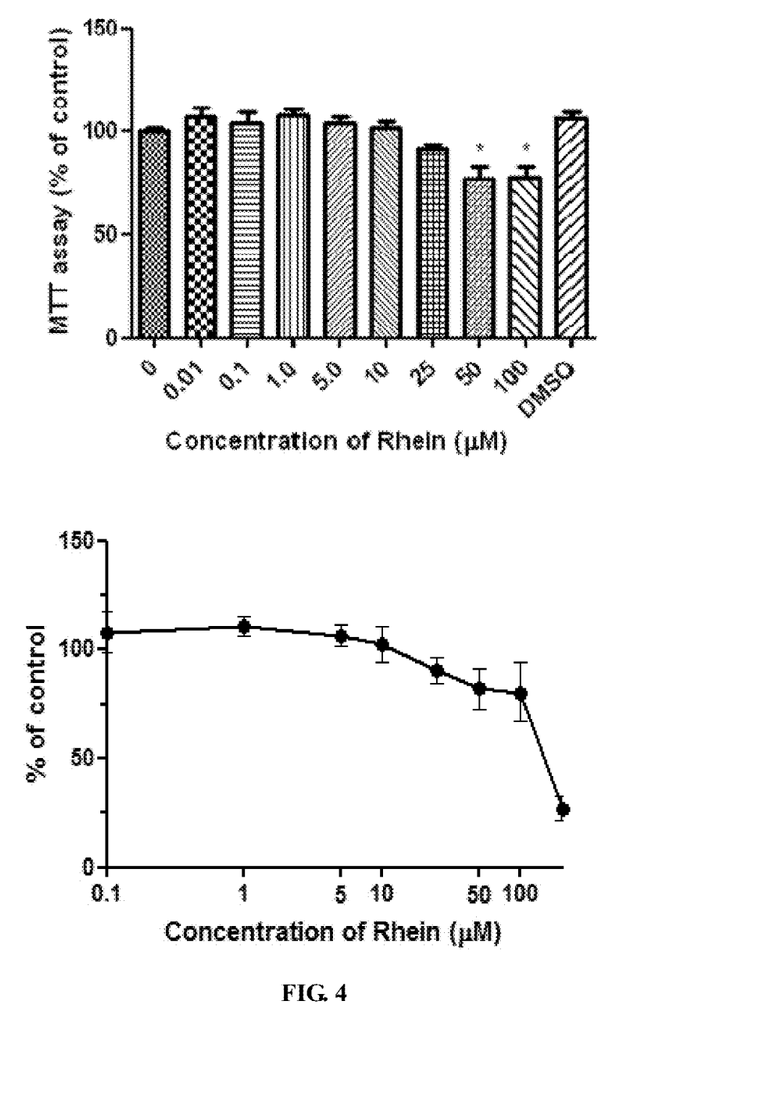
FIG. 4 shows the cytotoxicity of Rhein in the range of 0 to 200 μM in LTC-14 cells by means of MTT cell viability assay. The $LD_{50}$ of Rhein is approximately 130 μM.
Figure 5:
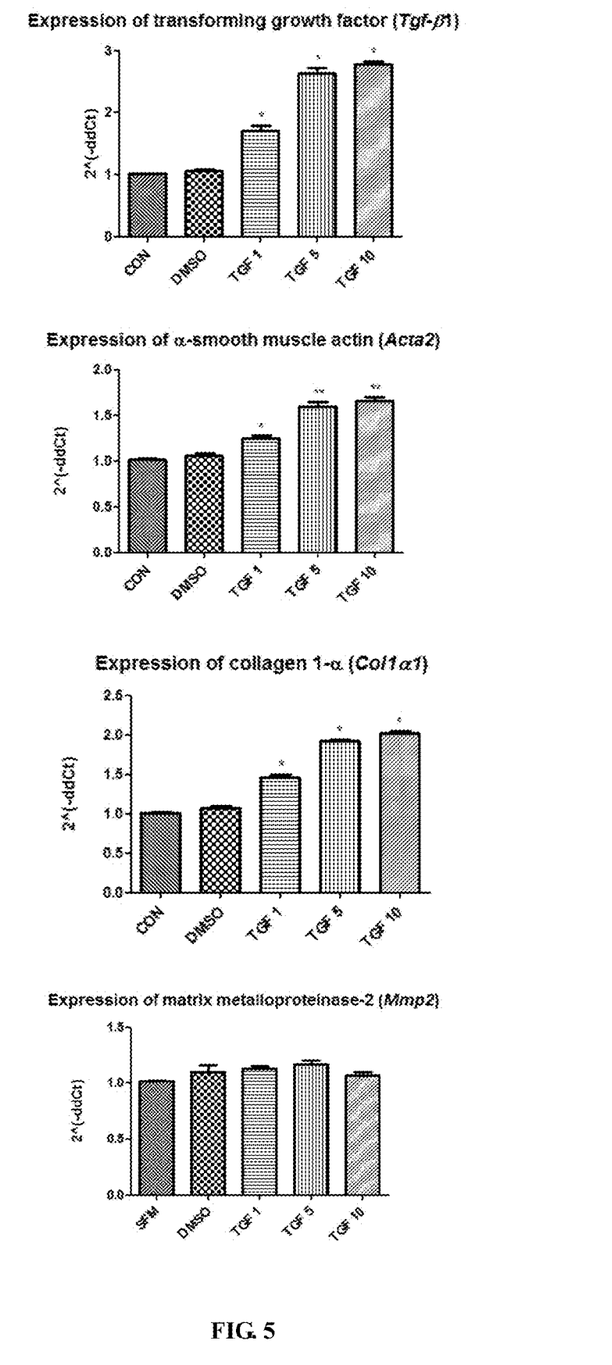
FIG. 5 shows the inductive effect of recombinant TGF-β at 1, 5 and 10 ng/mL in LTC-14 cells on mRNA expression of fibrogenic markers Tgf-β1, Acta2, Col I-α1 and Mmp2 by means of real-time PCR. TGF1, TGF5 and TGF10 respectively represent the concentrations of TGF-β given at 1, 5 and 10 ng/mL. A p-value of less than 0.05 is considered as statistically significant. *$p<0.05$ and **$p<0.01$ when comparing with serum-free medium (SFM) control.
Figure 6:
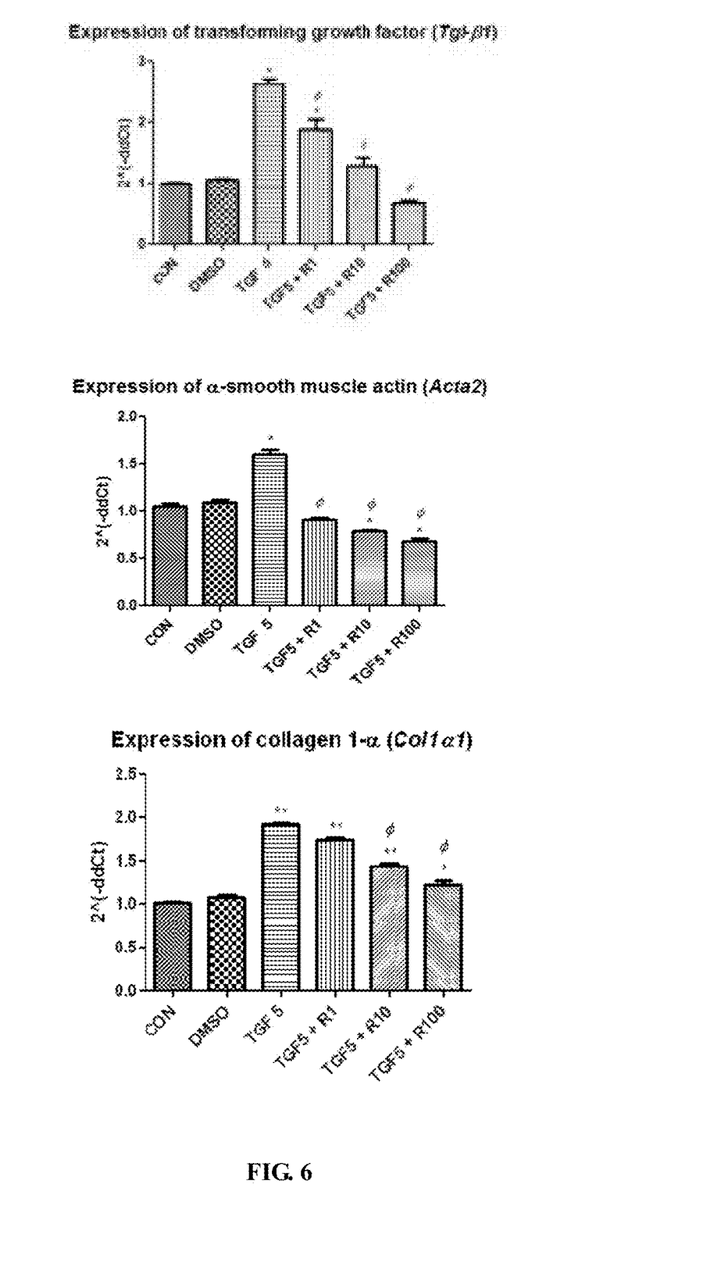
FIG. 6 shows the real-time PCR results of the suppressive effects of Rhein on different fibrogenic markers in TGF-β-stimulated LTC-14 cells (at 5 ng/mL of TGF-13). R1, R10 and R100 respectively represent the concentrations of Rhein given at 1, 10 and 100 μM. A p-value of less than 0.05 is considered as statistically significant. *$p<0.05$ and **$p<0.01$ when comparing with SFM control group whereas 0<0.05 comparing with TGF-β alone at 5 ng/mL (TGF 5).
Figure 7:
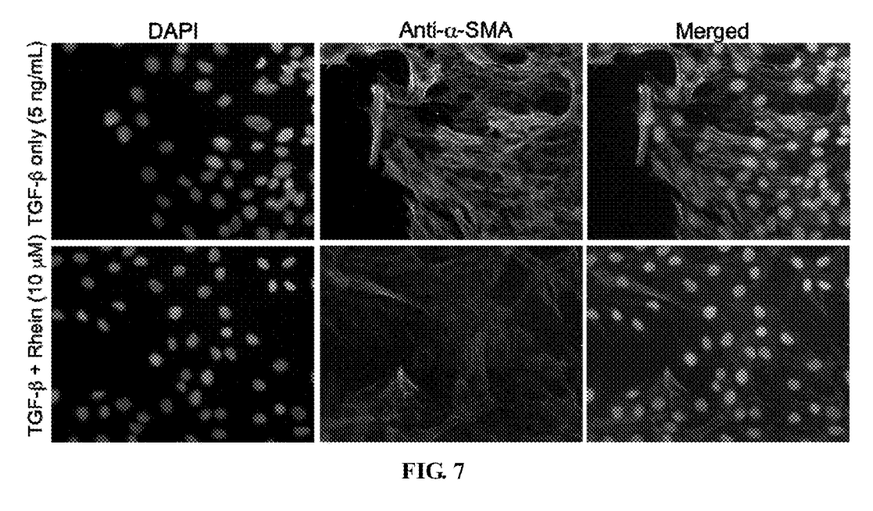
FIG. 7 shows the anti-fibrous effect of Rhein on α-SMA synthesis in TGF-β-stimulated LTC-14 cells by means of immunofluorescent staining DAPI staining indicates the number of nuclei whereas anti-α-SMA immunoreativity represents the expression of α-SMA.
Figure 8:
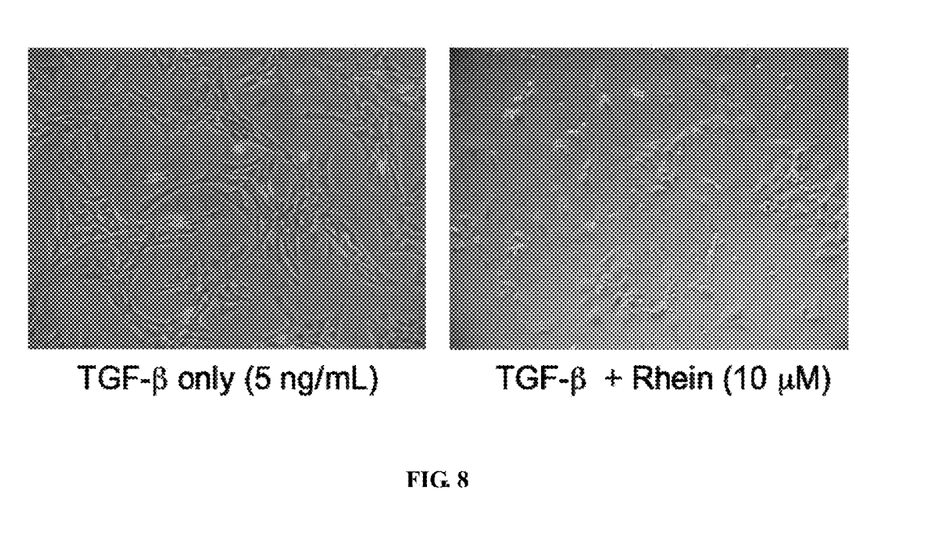
FIG. 8 shows that Rhein attenuates TGF-β-stimulated LTC-14 cells from transforming into myofibroblast-like phenotype.

Immunohistochemistry images reveal that the activation of PSCs is suppressed by Rhein as a substantial decrease of α-SMA expression is found in the pancreatic tissues of Rhein-treated CP mice when compared to that of the placebo-treated CP mice (FIGS. 3A and 3C). In addition, synthesis of ECM proteins, namely type I collagen and fibronectin are notably reduced by the administration of Rhein (FIGS. 3B and 3C). In the in vitro experiments, Rhein is demonstrated with its ability to suppress PSC proliferation and TGF-β-induced activation of PSCs in a dose-dependent manner. Upon stimulation with pivotal fibrotic mediator TGF-β, the application of Rhein remarkably suppresses the expression levels of various fibrogenic markers and extracellular matrix proteins including α-SMA (or Acta2), Tgf-β1, Col I-α1 and Fn1 (FIGS. 6 and 7). Further, Rhein represses the transformation of LTC-14 cells into myofibroblast-like phenotype (FIG. 8).

Cerulein-induced pancreatitis is an established and reproducible rodent model for studying pancreatic fibrosis. Repetitive injections of the CCK8 analogue cerulein over-stimulate the maturation of digestive enzymes and result in autodigestion and progressive scarring of the pancreatic parenchyma.

Experiments

C57BL6 mice at age of 6 to 8 weeks with body weight in the range of 20 to 24 grams were used in these experiments. Mice were randomly assigned into 5 groups. Control group received saline injections only; Rhein group was fed with Rhein (≥98% pure) dissolved in 0.5% sodium carboxymethyl cellulose (Sigma, USA) in a single dose of 0.4 mL at 50 mg/kg/day for 6 weeks; Cerulein group received 6 cerulein injections at 50 μg/kg three times a week for 6 weeks; Cer+Rh 6w group received cerulein injections same as Cerulein group plus oral gavage of a single dose of Rhein at 50 mg/kg/day from the first day of experimental period till the end in a total of 6 weeks; Cer+Rh 3w group received cerulein injections same as Cerulein group and Cer+Rh 6w group, but was given with Rhein at 50 mg/kg/day starting the first day of week 4 till the end of experiment in a total of 3 weeks (n=6/group). Upon scarification, pancreata were immediately removed, weighed, trimmed from fat and fixed in 4% paraformaldehyde-phosphate buffered saline (PBS) overnight at 4° C. Samples were then processed, embedded in paraffin wax, sectioned and subjected to Hematoxylin-eosin (H & E) staining or Sirius Red staining Levels of TNF-α· in animal serum samples were determined using commercial ELISA kits. Proteins extracted from pancreatic tissues were subjected to Western blotting analyses.

LTC-14 cells were cultured at 37° C. under a humidified condition of 95% air and 5% $CO_2$ in IMDM supplemented with 10% fetal bovine serum (FBS). Cells used in all the experiment were among passages 9 to 22. LTC-14 cells were seeded at a density of $1 \times 10^4$/well in a 96-well plate, and incubated with different concentrations of Rhein (dissolved in DMSO) for 24 hours. MTT reagent was added to the cells at the end of the 24-hour treatment period. After a 3-hour reaction time, MTT products were dissolved in DMSO and OD at 570 nm was taken.

When LTC-14 cells were incubated with recombinant TGF-β at 1, 5 and 10 ng/mL in IMDM supplemented with 0.2% FBS, mRNA expression of a series of fibrogenic markers namely Tgf-β1, Acta2, and Col1-α1, but not Mmp2, were found remarkably up-regulated. mRNA from each sample was extracted using Trizol reagent and subjected to a reverse transcription for cDNA synthesis. The synthesized cDNA template was applied to amplifications with rat-specific primers for Tgf-β1, Acta2, Col1-α1 and Mmp2 in a real-time PCR sequencer. Expression of the gene of interest was expressed as a Ct value and normalized to the internal control Gapdh.

Upon the stimulation of TGF-β at 5 ng/mL (TGF 5), Rhein at 1, 10 and 100 μM (R1, R10 and R100) significantly repressed the TGF-β-elevated mRNA expression levels of Tgf-β1, Acta2, and Col1-α1 in LTC-14 cells. After amplifications by real-time PCR, expression of the gene of interest was expressed as a Ct value and normalized to the internal control Gapdh.

To study the effect of Rhein on TGF-β induced expression of fibrotic filament formation, LTC-14 cells were grown on poly-L-lysine coated glass coverslips at a density of 1×10⁵ in a 24-well plate pre-incubated with TGF-β (5 ng/mL) for 24 hours before the treatment with or without Rhein (10 μM). At the time of harvest, cells were subjected to immunofluorescence assay for α-SMA immunoreactivities.

To study the effect of Rhein on TGF-β induced transformation of PSCs to myofibroblast-like cells, LTC-14 cells were grown at a density of 1×10⁵ in a 24-well plate, pre-incubated with TGF-β (5 ng/mL) for 24 hours and treated with or without Rhein (10 μM). At the time of harvest, cells were examined with morphological alterations under a light microscope.

Results

Expression of α-SMA

The oral administration of Rhein in a single dose at 50 mg/kg/day to cerulein-treated mice for 6 weeks significantly inhibits the expression of α-SMA in the pancreatic tissues. As a result, PSC activation is suppressed and the severity of fibrosis and CP is ameliorated. Results from real-time PCR and western blotting analyses are in accordance to the immunofluorescent images. Similar inhibition is also observed in the in vitro experiments.

Synthesis of Collagen

By means of Sirius Red staining, the amounts of collagenous protein produced upon tissue injury are notably reduced by Rhein in CP mice. Results from real-time PCR are in agreement with the Sirius Red staining data.

Production of Fibronectin

By means of Western blotting, the protein expression levels of fibronectin in CP mice treated with Rhein are remarkably decreased when comparing to those of non-Rhein-treated CP mice.

Expression of Fibrotic Mediators

In LTC-14 cells, the addition of recombinant TGF-β upregulates the expression levels of several pro-fibrotic markers such as α-SMA (or Acta2), TGF-β1, collagen I-α1 and Fn1. Application of Rhein suppresses TGF-β-stimulated expression levels of all these pro-fibrotic mediators.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

INDUSTRIAL APPLICABILITY

The compounds of the present invention, anthraquinone derivative 9,10-Dihydro-4,5-dihydroxy-9,10-dioxo-2-anthracenecarboxylic acid, also known as Rhein, are potent anti-fibrotic agent useful for preparation of a medicament to effectively treat fibrotic conditions or fibrotic related diseases. The present invention particularly relates to the suppression of pancreatic stellate cell activation for the management of chronic inflammatory, fibrotic and tumorigenic pathologies in the pancreas.

What is claimed is:

1. A method of treating pancreatic fibrosis in a human in need thereof comprising administering a therapeutically effective amount of a rhubarb extract to said human to treat the pancreatic fibrosis in the human.

2. The method of claim 1, wherein said rhubarb extract comprises a compound having formula (1):

having a chemical name of 9,10-Dihydro-4,5-dihydroxy-9,10-dioxo-2-anthracenecarboxylic acid.

3. The method according to claim 1 wherein the therapeutically effective amount is from 4.05 to 6.00 milligram/kilogram body weight/day to said human in at least one dose for a continuous duration of at least 3 weeks.

4. The method according to claim 1 wherein the composition is administered orally.

5. The method according to claim 1 wherein the pancreatic fibrosis is chronic pancreatitis.

* * * * *